United States Patent
Grossman et al.

[11] Patent Number: 5,915,384
[45] Date of Patent: Jun. 29, 1999

[54] MEDICAL BODY FLUID SAMPLER DEVICE

[76] Inventors: Michael D. Grossman, 6215 S. Iola Ct., Englewood, Colo. 80111; Jerome M. Eder, 21663 Ulmus Dr., Woodland Hills, Calif. 91364; Jewelanne Hurley, P.O. Box 10604, Burbank, Calif. 91510; Bernard Siegel, 838 N. Doheny Dr. Suite 805, West Hollywood, Calif. 90069; Kenneth Adelberg; Marvin Adelberg, both of 16821 Oak View Dr., Encino, Calif. 91436

[21] Appl. No.: 08/701,204

[22] Filed: Aug. 21, 1996

Related U.S. Application Data

[60] Continuation-in-part of application No. 08/293,380, Aug. 19, 1994, abandoned, which is a division of application No. 08/035,282, Mar. 22, 1993, Pat. No. 5,342,328.

[51] Int. Cl.$^6$ .................................................. A61B 5/00
[52] U.S. Cl. .......................... 128/760; 128/762; 128/767; 128/771; 604/317
[58] Field of Search .................................... 128/760, 761, 128/762, 763, 764, 765, 766, 767, 768, 769, 770, 771; 604/317–323; 606/120–124; 239/685; 222/185

[56] References Cited

U.S. PATENT DOCUMENTS

| | | | |
|---|---|---|---|
| 3,768,701 | 10/1973 | Leas et al. | 222/185 X |
| 4,548,362 | 10/1985 | Doering | 239/685 |
| 4,557,274 | 12/1985 | Cawood | 128/760 |
| 5,108,381 | 4/1992 | Kolozsi | 604/317 |
| 5,164,165 | 11/1992 | Butler | 222/185 X |
| 5,190,556 | 3/1993 | Hessel | 128/760 X |
| 5,211,642 | 5/1993 | Clendenning | 604/317 X |
| 5,222,631 | 6/1993 | Hood | 222/185 X |
| 5,380,289 | 1/1995 | Hemstreet et al. | 604/317 |
| 5,415,665 | 5/1995 | Hessel et al. | 128/764 X |

*Primary Examiner*—Mary Beth Jones
*Attorney, Agent, or Firm*—Edward A. Sokolski

[57] ABSTRACT

A container has an upper fluid receiving portion and a lower fluid discharge portion which is closed off at its bottom by a closure. In carrying out the method of the invention, a blood sampling from the umbilical cord of a newly born infant is taken by first clamping off a section of the cord. The clamped section is then separated from the main portion of the cord and deposited into the container. One of the clamps is then removed to permit the blood in the cord section to drain into the container. The drained blood is then transferred to a second container, which may comprise a test tube or syringe, through the fluid discharge portion of the container, this being achieved by either causing a needle attached to the container and sealed with a needle cover to penetrate the needle cover as well as the test tube cover, penetrating the closure with a needle if it be a diaphragm or the like or opening a valve at such closure by a mechanical actuation with the nose of a syringe. The needles employed are protected by shielding hoods to prevent accidental needle sticking.

13 Claims, 6 Drawing Sheets

FIG. I

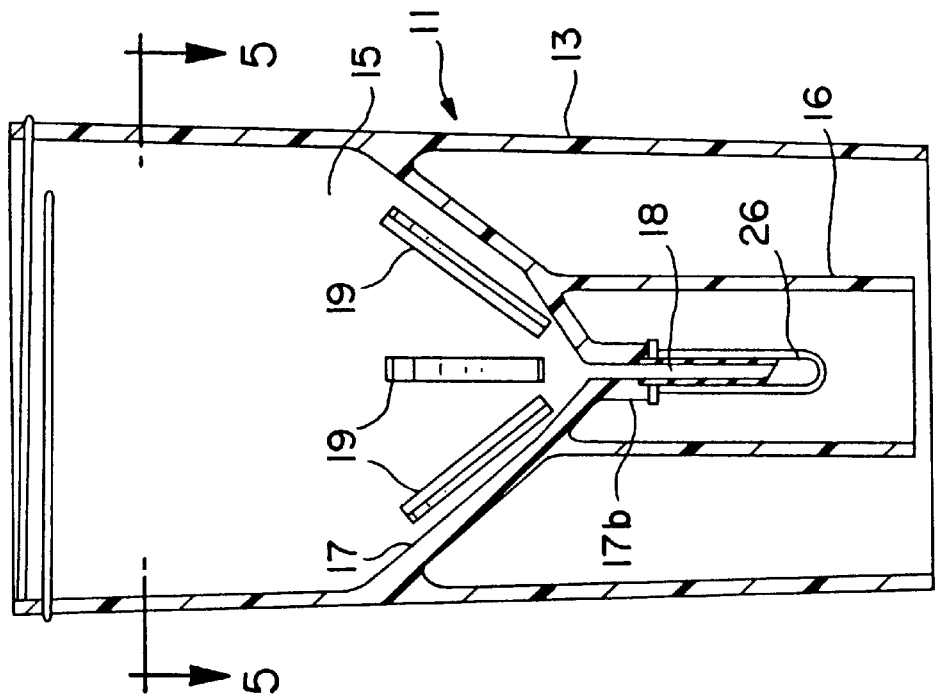
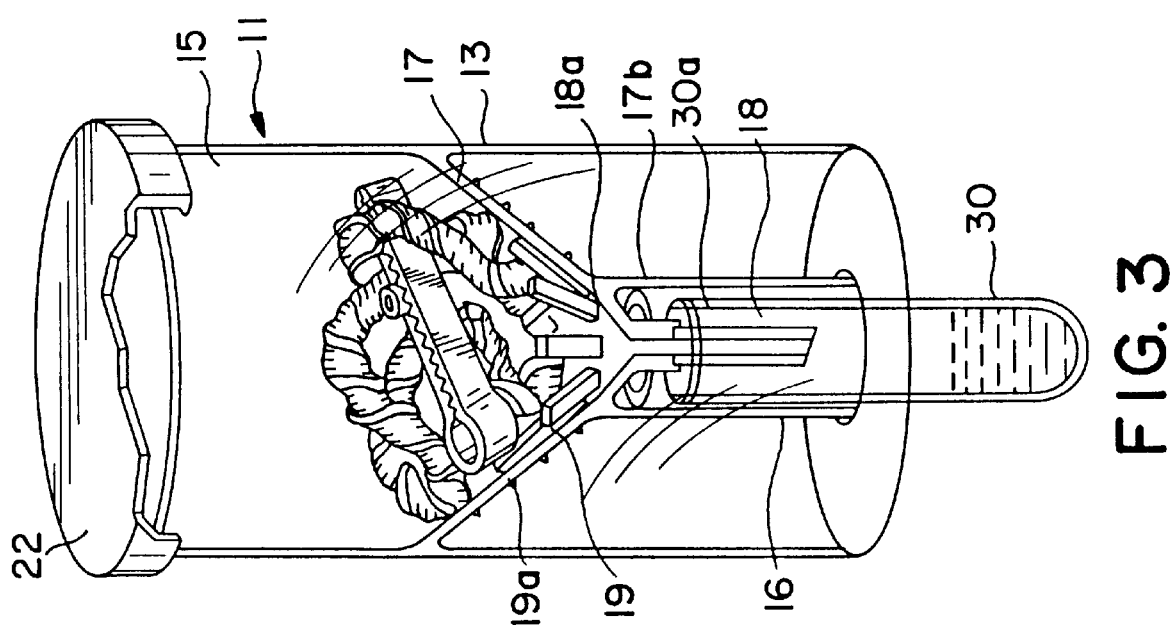

MEDICAL BODY FLUID SAMPLER DEVICE

This application is a Continuation in Part of application Ser. No. 08/293,380 filed Aug. 19, 1994, now abandoned, which in turn is a Divisional of application Ser. No. 08/035,282 filed Mar. 22, 1993, now U.S. Pat. No. 5,342,328.

BACKGROUND OF THE INVENTION

1. Field of the Invention

This invention pertains to medical body fluid sampler devices and methods and more particularly to such a device and method employing a container for collecting such fluid from which the fluid can be transferred to another container with minimum risk of infection from contacting said fluid to the personnel involved.

2. Description of the Prior Art

Body fluid samplings are often medically required such as in the case of the sampling of the umbilical cord blood of a newborn infant to ascertain blood type and Rh factor. This is generally accomplished by inserting a large bore bare hypodermic needle attached to a syringe into the vein of the umbilical cord which has just been separated from the infant but usually still attached to the placenta. The typical minimal volume of blood required is approximately 5 cc. This blood sample is then transferred to a test tube which is stoppered with a rubber stopper.

In an alternate sampling method employed in the prior art, the just severed free end of the umbilical cord, usually while still attached to the placenta, is held over the opening of a test tube and the cord blood permitted or caused to flow into the open topped tube which is then generally closed with a rubber stopper.

With both of these prior art methods, the blood being sampled is liable to come into contact with members of the delivery team. This presents the hazard of exposure to blood which may be contaminated with viral or bacterial diseases. Dangerous and potentially fatal viral infections such as the human immunodeficiency viruses which leads to AIDS, hepatitis B and C, among others have occurred in hospital personnel after exposure to contaminated blood.

SUMMARY OF THE INVENTION

The present invention minimizes the aforesaid risks of infection to medical personnel by contaminated blood and other body fluids when taking fluid samples. This end result is achieved in the case of umbilical cord blood sampling, by first clamping off a section of cord, which typically is 12–16 cm in length, with a pair of medical clamps. This clamped section is then separated from the remainder of the umbilical cord and deposited into a unique container which is free standing and has an upper receiving portion and a lower fluid discharge portion which is closed off by a closed discharge port. The blood is deposited into the upper portion of the container by removing one of the clamps which removal permits the blood to drain from the cord into the container. This blood is then transferred to a second container which may comprise an open end tube such as a test tube or a syringe. This transfer operation is achieved by either having a hooded needle attached to the discharge port penetrate an evacuated vial or conventional vial or penetrating the closed port with a needle if it be formed by a diaphragm or the like or opening a valve at such port by a mechanical actuation. This is accomplished without the need for the operator to touch the needle or the valve mechanism as the case may be.

Such sequencing in carrying out the method of the invention permits the subsequent use of a pressure difference, obtained by utilizing an evacuated, stoppered tube, to transfer the desired blood sample to a sealed second container, again without exposing the operator to the possibility of blood contact.

To appreciate the significance of the sequencing in carrying out the method of the invention, it should be noted that a pressure difference of ¼ to ¾ atmosphere is required to transfer blood through a hyperdermic needle of size 17–23 gage within a reasonable period of time, i.e. less than 15 seconds. In the methods of the prior art, the sampling is or may be accomplished by utilizing a hyperdermic needle attached to a syringe and drawing off the desired volume of blood directly from the umbilical cord. Unfortunately, this method has the disadvantage of having the potential of sticking the operator with a bloody needle, or otherwise exposing the operator to blood.

The method of the present invention utilizes a similar pressure difference and hyperdermic needle but because of the sequencing and use of gravity flow, the risk of needle stick is eliminated. This is achieved as follows:

After the umbilical cord is clamped, sectioned, placed in a receiving container and then unclamped, gravity, but no other induced pressure difference, is permitted to enhance the flow of blood as the cord section naturally contracts to expel the blood contained therein, through the newly cut ends of the veins and artery.

With the method of the invention, the blood is permitted to pool in a collection device having a special access built in which is compatible with a second device which is essentially a transfer/holding tube, neither device presenting the potential of exposed blood or an exposed blood covered hyperdermic needle.

It is therefore an object of this invention to minimize the hazard of infection to medical personnel in their taking blood or other body fluid samples.

Other objects of the invention will become apparent from the following description in conjunction with the accompanying drawings.

BRIEF DESCRIPTION OF THE DRAWINGS

FIG. 3 is a perspective view illustrating the use of the preferred embodiment of the device of the invention in carrying out a still further step of the preferred embodiment;

FIG. 4 is a cross section view of the preferred embodiment of the device of the invention;

DETAILED DESCRIPTION OF THE INVENTION

Figure 1:
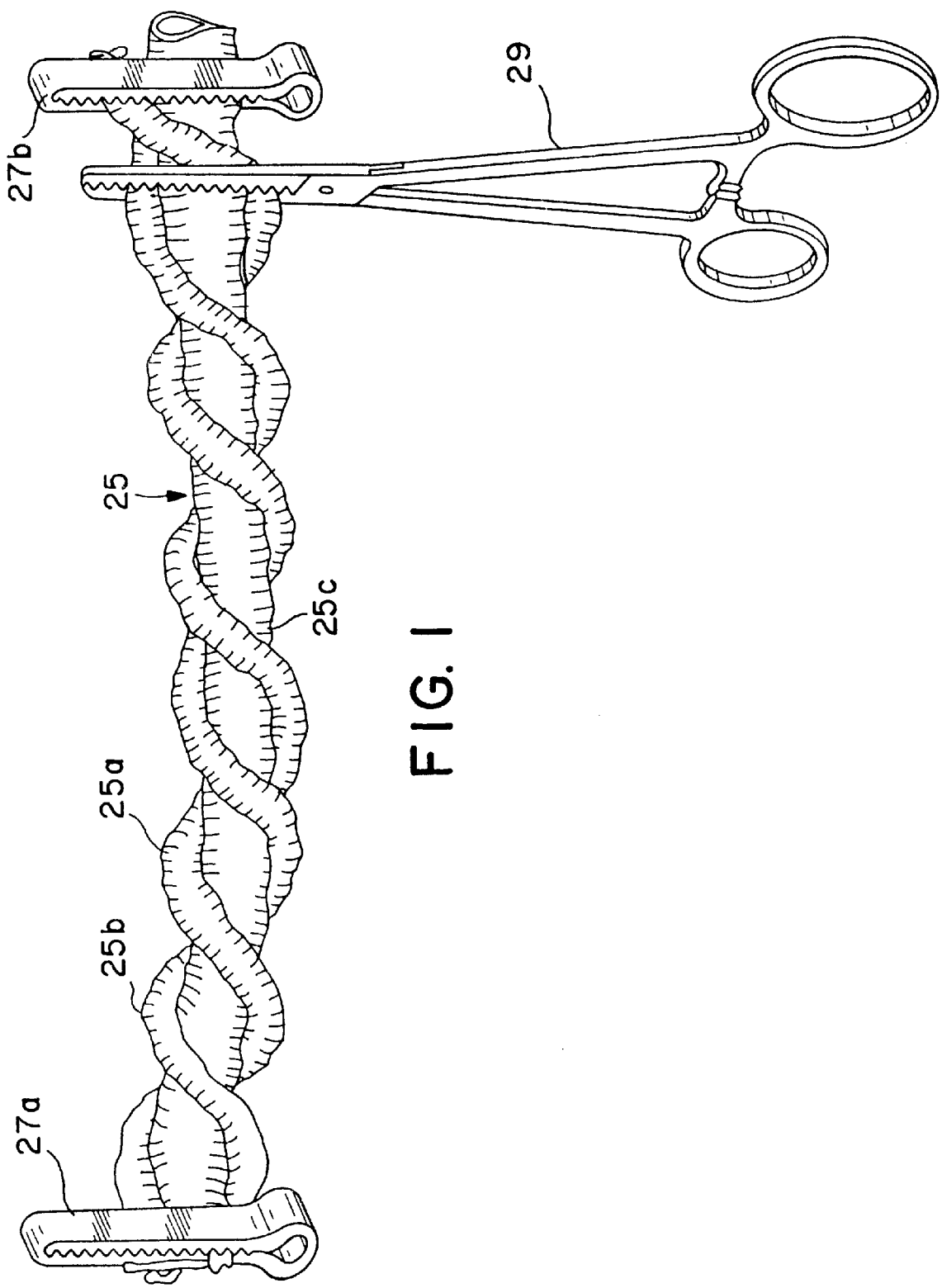
FIG. 1 is a perspective view illustrating one of the steps in carrying out the preferred embodiment of the method of the invention.

Referring now to FIGS. 2–5, a preferred embodiment of the device of the invention is illustrated. Container 11 has a cylindrical outer wall 13 and is self supporting or freestanding. The container has an upper fluid receiving portion 15 and a lower portion including a port 17b, needle 18 and needle hood 16. Fluid receiving portion 15 has a conically shaped bottom portion 17 in the form of a funnel. A plurality of fluid level markers 17a run circumferentially around bottom portion 17 which may be raised portions on the interior as shown, may be on the exterior or may be inscribed in bottom portion 17.

Installed in the narrow cylindrical outlet portion 17b of funnel shaped bottom portion 17 is a hollow needle member 18. This 6 needle member is installed with its outer walls in fluid tight relationship to the inner walls of outlet portion 17b. A rubber sleeve 26 is fitted over needle 18 to seal off the needle. Axial rib members 19 of varying height or thickness for supporting nonliquid material in the container are installed in bottom portion 17 at a location spaced upwardly from outlet portion 17b. Said support member may also consist of a flat strainer-like surface with perforations. A cap 22 is provided for the top of the container.

The preferred embodiment is fabricated of a clear or translucent plastic to permit viewing of the accumulated blood level in the funnel shaped portion 17 of the container. However, the device could be made of an opaque material provided that a viewing window is provided to permit observation of this blood level.

Figure 2:
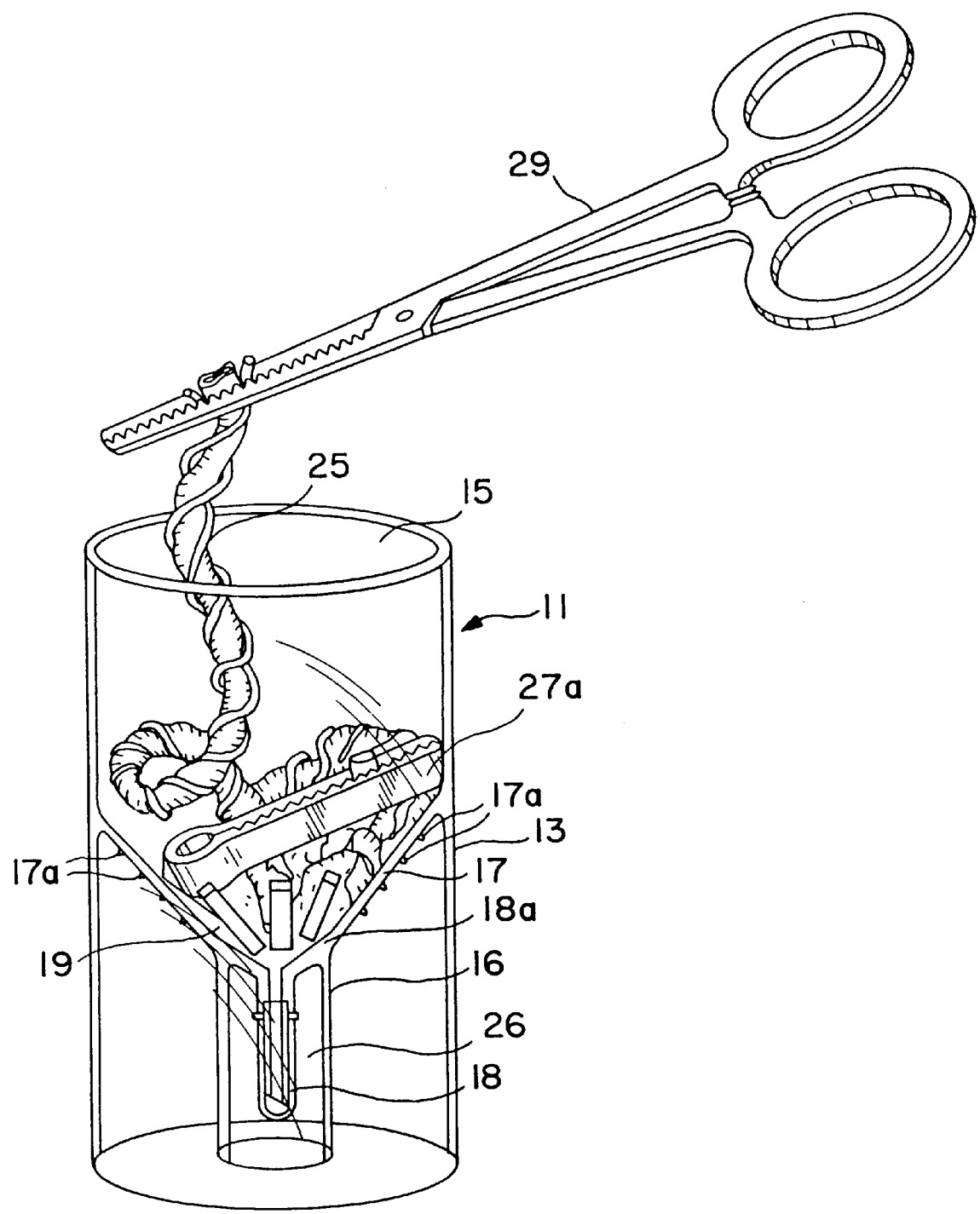
FIG. 2 is a perspective view illustrating the use of a preferred embodiment of the device of the invention in carrying out a further step of the preferred embodiment of the method of the invention.
Figure 5:
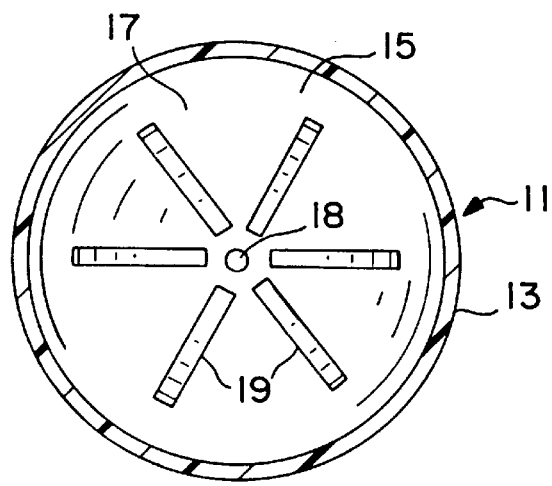
FIG. 5 is a cross sectional view taken along the plane indicated by 5—5 in FIG. 4.

Referring now to FIGS. 1–3, the method of the invention is illustrated. As shown in FIG. 1, a length of umbilical cord 25 which comprises a pair of veins 25a and 25b and an artery 25c is clamped off with a pair of surgical clamps 27a and 27b. A length of cord 25 which usually is 8–30 cm and preferably 12–16 cm has been found to be satisfactory to provide an adequate blood sampling in most cases. The end of the umbilical cord towards the infant is then severed next to clamp 27a, removing this side of the clamped off section from the main portion of the umbilical cord. A hemostat 29 is then clamped to the end of the clamped off section towards the placenta, close to clamp 27b. The clamped cord section is then severed between the hemostat and clamp 27b. The clamped section of cord with its opposite end still being clamped by clamp 27a is then placed in the fluid receiving end 15 of the container usually by means of hemostat 29, as shown in FIG. 2. On the chance the section of the cord contains blood under some pressure, the end of the cord is pointed toward the cup interior prior to release of the clamp.

The hemostat is then removed from the cord and lid 22 placed on the container. The blood in the umbilical cord will flow into the container and when a sufficient amount of blood has pooled, an evacuated and stoppered tube 30 having an elastic cover 30a is inserted into the fluid discharge portion 16 of the container, as shown in FIG. 3. With such insertion the needle 18 penetrates both its own elastic sleeve 26 and the elastic stopper 30a of the test tube, permitting the blood to flow into the hooded test tube. Suitable tube devices which may be used as test tube 30 include the Vacutainer which is commercially available from Becton Dickenson, Inc. and the Venoject available from Terumo, Inc. When a sufficient quantity of the blood in the container has flowed into the tube device, the tube is removed and the elastic sleeve 26 reseals the needle tip. Suitable testing of the blood sample may then be made. The inner surfaces of the container and the needle may be coated with an anticoagulant such as Heparin to avoid clotting of the blood, or this anticoagulant may be added prior to use.

Figure 6:
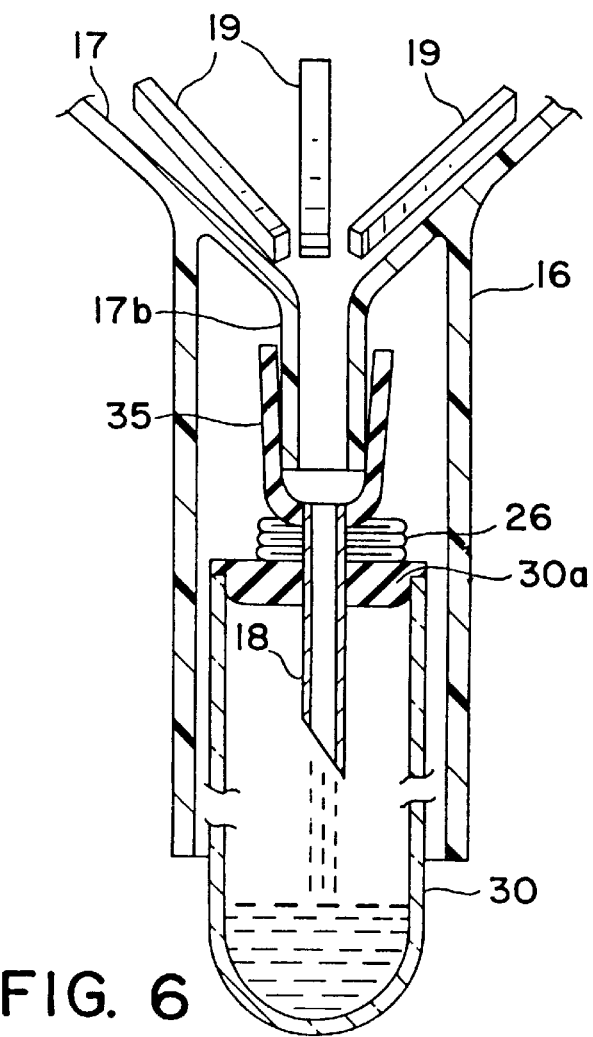
FIG. 6 is a cross sectional view of a second embodiment of the fluid discharge portion of the device of the invention while being utilized in discharging fluid to the second container.
Figure 7:
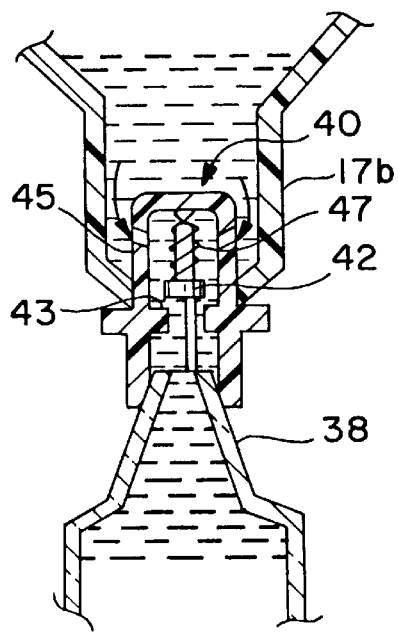
FIG. 7 is a cross sectional view of a third embodiment of the fluid discharge-portion of the device of the invention while being utilized in discharging fluid to the second container.
Figure 8:
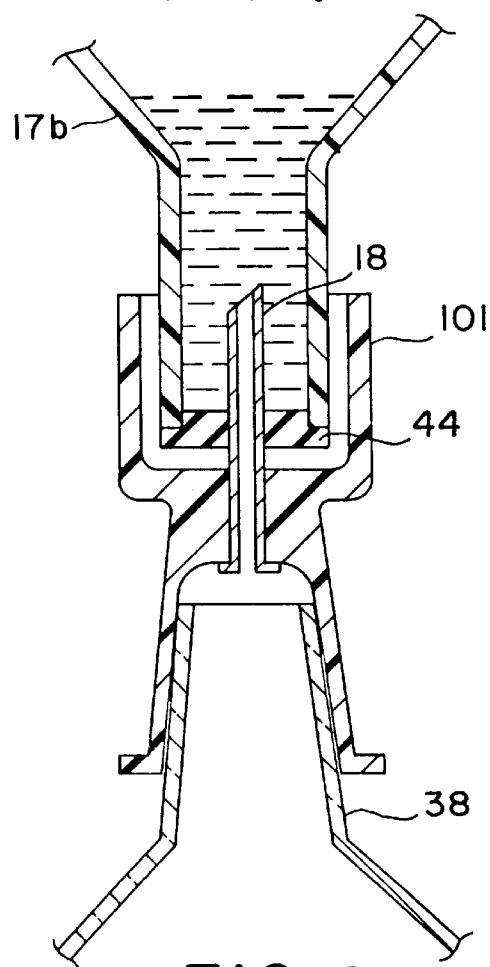
FIG. 8 is a cross sectional view of a fourth embodiment of the fluid discharge portion of the device of the invention while being utilized in discharging fluid to the second container.

Referring now to FIGS. 6–8, alternative devices which may be utilized in discharging the fluid are illustrated.

Figure 9:
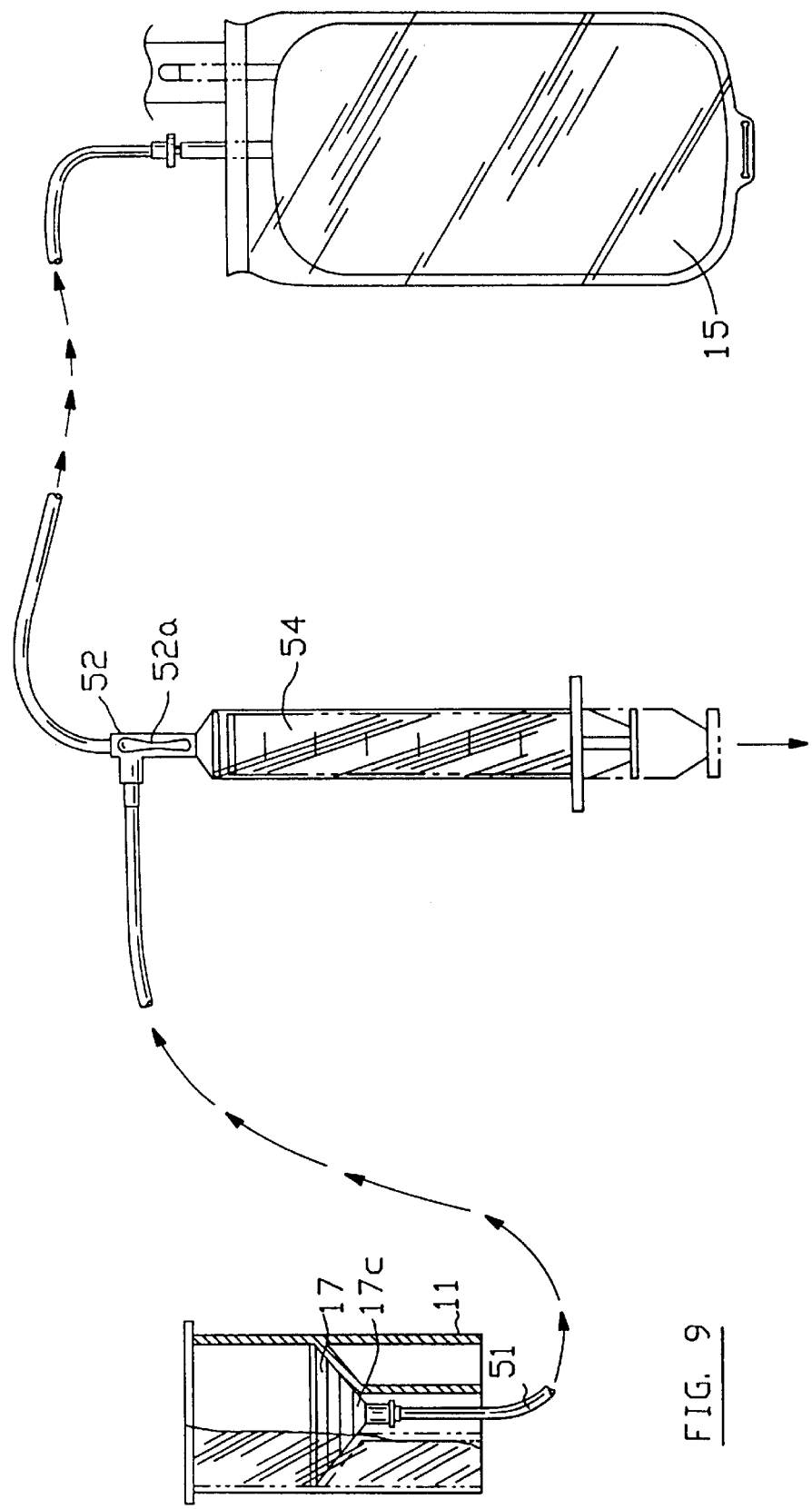
FIG. 9 is a top front perspective view illustrating a fifth embodiment of the invention.

Referring now to FIG. 9, a fifth embodiment of the invention is illustrated. In this embodiment, the blood is drawn away from the bottom of the container 11 by means of an extension tube with the blood being controllably fed to a syringe.

Extension tube 51 is connected to the output 17c of funnel shaped container 17. The distal end of extension tube 51 is connected to 3-way stopcock valve 52 which has a control arm 52a for use in alternatively connecting tube 51 to syringe 54, connecting syringe 54 to blood collection bag 55, and shutting off flow from tube 51. Thus larger amounts of blood can be either taken by successively filling the syringe and collection bag. The blood can thus be collected at a location away from the container 11. In this manner, the blood can more readily be dispensed in a controlled manner and larger quantities of blood handled.

In the embodiment of FIG. 6, a conventional needle-hub arrangement includes a needle 18 and a hub 35 which is integrally combined therewith. The hub is tightly secured on the end portion 17b of the funnel shaped container portion 17 by means of a press tight fit and, if necessary, cementing. The needle has a rubber sleeve 26 securely fitted thereon. The rubber sleeve 26 is shown in FIG. 6 in its collapsed condition. Operation is similar to that of the preferred embodiment in conjunction with a Vacutainer or the like, with the sleeve 26 as well as the stopper 30a on the Vacutainer being penetrated by the needle on its insertion into the hooded fluid discharge portion 16 of the container.

In the embodiment of FIG. 7, the outlet of the discharge member 17b has a normally closed poppet valve mechanism 40 integrally formed therewith. This valve includes a moveable seal which seats on shoulder 43 and is biased in this position by means of spring 47. This poppet valve is actuated by syringe tip 38, permitting the blood to flow through opening 45 in the valve and into the syringe as shown in the Figure.

The embodiment of FIG. 8 utilizes a conventional syringe 38 with an attached hooded needle 18. The hooded needle mates with the blood collection port 17b, and flow is possible once the needle 18 penetrates the diaphragm 44 integral with the blood port 17b.

As illustrated in FIGS. 2, 3, 4, 6, and 8, the end of the needle is surrounded by a longer hood which prevents the needle from inadvertently sticking the user's fingers or other body surface. Moreover, fluid transfer is possible only after a sealed connection is made between the receiving container and the second transfer container.

While the invention has been described and illustrated in detail, it is to be clearly understood that this is intended by way of illustration and example only and not by way of limitation, the scope of the invention being limited only by the terms of the following claims.

I claim:

1. A system for use in receiving a sample of human tissue containing body fluid, separating said fluid from said tissue and dispensing said fluid comprising:

a first container, said first container being at ambient atmospheric pressure, said first container having an upper receiving portion with an open top for receiving said tissue sample and including means for separating the fluid from the tissue sample in said receiving portion solely by gravity flow and without any filtering of the fluid, said first container further having a lower fluid discharge portion in fluid communication with said upper receiving portion, there being no liquid filter between said lower fluid discharge portion and said upper receiving portion for filtering out particles from said fluid, a second container connected to said first container, and a normally closed off port connected to the lower discharge portion and located between the lower discharge portion and said second container for preventing the separated fluid from entering said second container, said normally closed off port initially sealing off flow of fluid from said first container to said second container and being adapted to be opened in response to a mechanical actuation to release said fluid to said second container, said second container receiving and retaining said fluid for later analysis, whereby the likelihood of contact between said fluid and the hands and fingers of the user of said system is minimized.

2. The container of claim 1 wherein the bottom portion of said receiving portion is funnel shaped and has a downwardly convergent tapered wall.

3. The container of claim 1 wherein at least a portion of said container is fabricated of a light passing material thereby enabling viewing of the level of the fluid in said first container.

4. The container of claim 1 wherein the bottom portion of the container has one or more markers thereon to indicate the fluid level.

5. A container for use in receiving a sample of human tissue containing body fluid, separating said fluid from said tissue and dispensing said fluid to a second container comprising:

an upper receiving portion having an open top for receiving said tissue sample, and including means for separating the fluid from the tissue sample in said receiving portion by gravity flow, a support for supporting non-liquid material mounted in said receiving portion at a location spaced from the bottom end thereof, a lower fluid discharge portion in fluid communication with said upper receiving portion, and a closed off port located in the lower discharge portion for retaining the separated fluid in said container, said closed off port initially sealing off flow of fluid from said container to said second container and being adapted to be opened in response to a mechanical actuation to release said fluid to said second container, whereby the likelihood of contact between said fluid and the hands and fingers of the user of said container is minimized.

6. A container for use in receiving a sample of human tissue containing body fluid, separating said fluid from said tissue and dispensing said fluid to a second container comprising:

an upper receiving portion having an open top for receiving said tissue sample, and including means for separating the fluid from the tissue sample in said receiving portion by gravity flow, a lower fluid discharge portion in fluid communication with said upper receiving portion, and a closed off port comprising a hollow needle and a flexible liquid tight sleeve installed thereover located in the lower discharge portion for retaining the separated fluid in said container, said closed off port initially sealing off flow of fluid from said container to said second container and being adapted to be opened in response to a mechanical actuation to release said fluid to said second container, said lower discharge portion including a hood surrounding said needle to prevent inadvertent needle sticking of the user, whereby the likelihood of contact between said fluid and the hands and fingers of the user of said container is minimized.

7. A container for use in receiving a sample of human tissue containing body fluid, separating said fluid from said tissue and dispensing said fluid to a second container comprising:

an upper receiving portion having an open top for receiving said tissue sample, and including means for separating the fluid from the tissue sample in said receiving portion by gravity flow, a lower fluid discharge portion in fluid communication with said upper receiving portion, and a closed off port comprising a poppet valve adapted for mechanical actuation located in the lower discharge portion for retaining the separated fluid in said container, said closed off port initially sealing off flow of fluid from said container to said second container and being adapted to be opened in response to a mechanical actuation to release said fluid to said second container, whereby the likelihood of contact between said fluid and the hands and fingers of the user of said container is minimized.

8. A container for use in receiving a sample of human tissue containing body fluid, separating said fluid from said tissue and dispensing said fluid to a second container comprising:

an upper receiving portion having an open top for receiving said tissue sample, and including means for separating the fluid from the tissue sample in said receiving portion by gravity flow, a lower fluid discharge portion in fluid communication with said upper receiving portion, and a closed off port comprising a vacuum actuated valve located in the lower discharge portion for retaining the separated fluid in said container, said closed off port initially sealing off flow of fluid from said container to said second container and being adapted to be opened in response to a mechanical actuation to release said fluid to said second container, whereby the likelihood of contact between said fluid and the hands and fingers of the user of said container is minimized.

9. A container for use in receiving a sample of human tissue containing body fluid, separating said fluid from said tissue and dispensing said fluid to a second container comprising:

An upper receiving portion having an open top for receiving said tissue sample, and including means for separating the fluid from the tissue sample in said receiving portion by gravity flow, a lower fluid discharge portion in fluid communication with said upper receiving portion, and a closed off portion comprising a puncturable self-sealing diaphragm located in the lower discharge portion for retaining the separated fluid in said container, said closed off portion initially sealing off flow of fluid from said container to said second container and being adapted to be opened in response to a mechanical actuation to release said fluid to said second container, whereby the likelihood of contact between said fluid and the hands and fingers of the user of said container is minimized.

10. A system for use in receiving a sample of human tissue containing body fluid, separating said fluid from said tissue and dispensing said fluid comprising:

a first container, said first container having an upper receiving portion with an open top for receiving said tissue sample and including means for separating the fluid from the tissue sample in said receiving portion by gravity flow, said first container further having a lower discharge portion in fluid communication with said upper receiving portion, a second container connected to said first container, and a normally closed off port formed by a hollow needle having a flexible liquid tight sleeve installed thereover, said port being located in the lower discharge portion for retaining the separated fluid in said second container, said normally closed off port initially sealing off flow of fluid from said first container to said second container and being adapted to be opened in response to a mechanical actuation to release said fluid to said second container, said second container receiving and retaining said fluid for later analysis, whereby the likelihood of contact between said fluid and the hands and finger of the user of said system is minimized.

11. The system of claim 1 wherein said second container comprises a syringe, an extension tube connecting said syringe to said first container, said normally closed off port comprising a manually actuable valve interposed between said extension tube and said syringe.

12. The system of claim 11 and further including a blood collection bag connected to said valve.

13. A system for use in receiving a sample of human tissue containing body fluid, separating said fluid from said tissue and dispensing said fluid to a second container comprising:

a first container having an upper receiving portion with an open top for receiving said tissue sample and including means for separating the fluid from the tissue sample by gravity flow, a lower discharge portion in fluid communications with said upper receiving portion, a second container separated from said first container, an extension tube connected on one end thereof to said lower discharge portion to receive the output thereof, a manually actuable valve connected to the other end of said extension tube, said second container being connected to said valve, said valve being manually actuable to alternatively, connect said extension tube to said second container or disconnect said extension tube from said second container.

* * * * *